United States Patent
Young

(10) Patent No.: US 10,994,080 B2
(45) Date of Patent: May 4, 2021

(54) AUTOINJECTOR WITH RETRACTING NEEDLE

(71) Applicant: Oval Medical Technologies Limited, Cambridge (GB)

(72) Inventor: Matthew Young, Cambridge (GB)

(73) Assignee: OVAL MEDICAL TECHNOLOGIES LIMITED, Cambridge (GB)

( * ) Notice: Subject to any disclaimer, the term of this patent is extended or adjusted under 35 U.S.C. 154(b) by 306 days.

(21) Appl. No.: 16/061,273

(22) PCT Filed: Dec. 9, 2016

(86) PCT No.: PCT/GB2016/053904
§ 371 (c)(1),
(2) Date: Jun. 11, 2018

(87) PCT Pub. No.: WO2017/098277
PCT Pub. Date: Jun. 15, 2017

(65) Prior Publication Data
US 2018/0361078 A1 Dec. 20, 2018

(30) Foreign Application Priority Data

Dec. 11, 2015 (GB) .................................... 1521883

(51) Int. Cl.
*A61M 5/32* (2006.01)
*A61M 5/20* (2006.01)
*A61M 5/24* (2006.01)

(52) U.S. Cl.
CPC .......... *A61M 5/326* (2013.01); *A61M 5/2033* (2013.01); *A61M 5/2466* (2013.01); *A61M 2205/13* (2013.01)

(58) Field of Classification Search
CPC .. A61M 5/326; A61M 5/2033; A61M 5/2466; A61M 2205/13

(Continued)

(56) References Cited

U.S. PATENT DOCUMENTS

2003/0105430 A1 6/2003 Lavi et al.
2006/0069354 A1 3/2006 Buenger et al.
(Continued)

FOREIGN PATENT DOCUMENTS

AU 2014277752 1/2015
CN 1443080 9/2003
(Continued)

OTHER PUBLICATIONS

International Search Report and Written Opinion issued in International Application No. PCT/GB2016/053904 dated Mar. 20, 2017 (14 pages).

(Continued)

*Primary Examiner* — Phillip A Gray
(74) *Attorney, Agent, or Firm* — Hamre, Schumann, Mueller & Larson, P.C.

(57) ABSTRACT

An automatic drug delivery device is described, comprising: a housing (1); a skin sensor element (15) coupled to the housing and movable relative to the housing, wherein the skin sensor element is biased into a front position relative to the housing and is movable to a rear position relative to the housing when the skin sensor element is pressed against an injection site; a needle assembly comprising a hypodermic needle (11), the hypodermic needle extending outside of the housing when the device is in a needle insertion configuration; a drug delivery mechanism comprising a stored energy source (4), within the housing; wherein the drug delivery mechanism is released when the skin sensor element is moved from the front position towards the rear position and wherein the stored energy source is arranged to expand along an axis that is offset from an axis of travel of the needle assembly in use; a needle retraction mechanism configured to withdraw the hypodermic needle into the housing when the needle retraction mechanism is released;

(Continued)

wherein the needle retraction mechanism is coupled to the skin sensor element such that when the skin sensor element is moved from the rear position towards the front position, and the needle is in the needle insertion position, the needle retraction mechanism is released.

37 Claims, 16 Drawing Sheets

(58) Field of Classification Search
USPC .................................................. 604/198
See application file for complete search history.

(56) References Cited

U.S. PATENT DOCUMENTS

| | | | |
|---|---|---|---|
| 2010/0137801 | A1 | 6/2010 | Streit et al. |
| 2011/0224620 | A1* | 9/2011 | Johansen ............ A61M 5/2033 604/192 |
| 2013/0317479 | A1 | 11/2013 | Brereton et al. |

FOREIGN PATENT DOCUMENTS

| | | |
|---|---|---|
| CN | 1585655 | 2/2005 |
| CN | 1713930 | 12/2005 |
| CN | 1861208 | 11/2006 |
| CN | 1909939 | 2/2007 |
| CN | 101420995 | 4/2009 |
| CN | 102083486 | 6/2011 |
| CN | 103118723 | 5/2013 |
| CN | 104066466 | 9/2014 |
| CN | 104968381 | 10/2015 |
| CN | 107106787 | 8/2017 |
| EP | 2399630 | 12/2011 |
| EP | 2596823 | 5/2013 |
| FR | 2616221 | 12/1988 |
| JP | 2014-528787 | 10/2014 |
| JP | 2015-530170 | 10/2015 |
| WO | 2009062508 | 5/2009 |
| WO | 2013065597 | 5/2013 |
| WO | 2015/015170 | 2/2015 |

OTHER PUBLICATIONS

Great Britain Search Report issued in Great Britain application No. GB 1521883.7 dated May 12, 2016 (4 pages).
First Office Action issued for Chinese Patent Application No. 201680072448.1, dated Jun. 18, 2020, 13 pages including English translation.
Office Action issued for the Japanese patent application No. 2018-530589, dated Dec. 8, 2020, 13 pages including English translation.

* cited by examiner

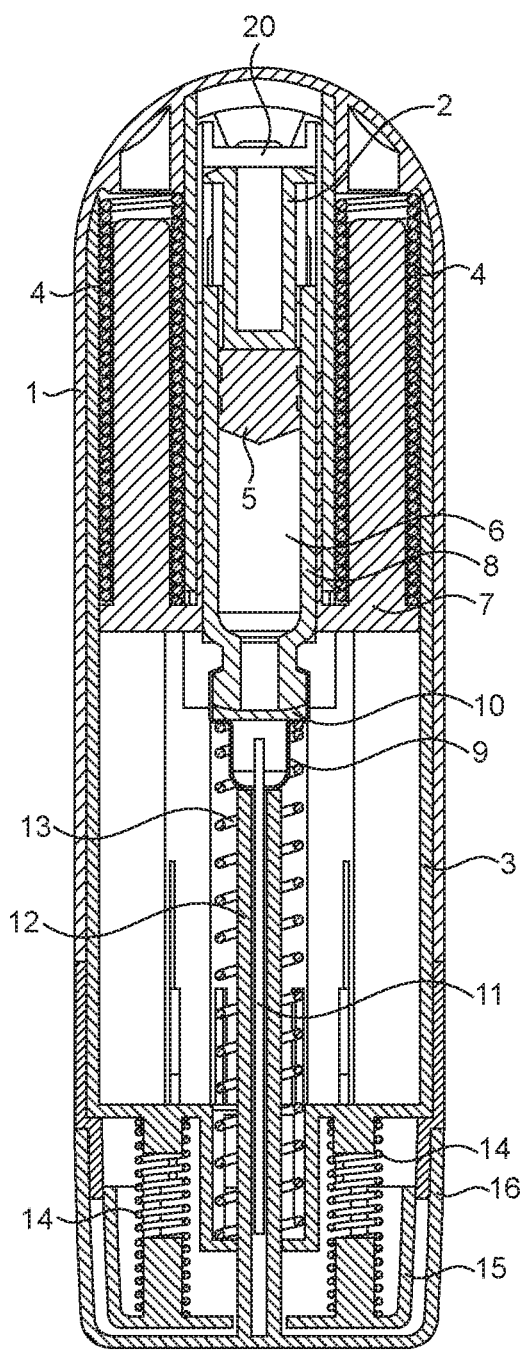
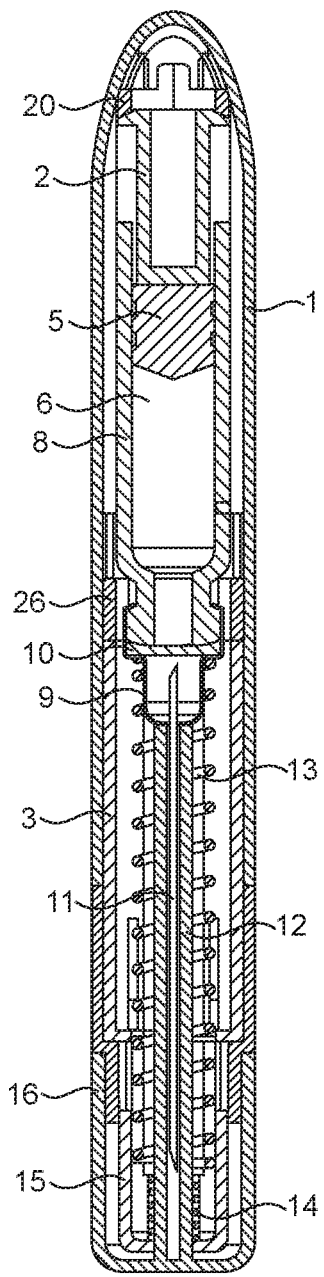
FIG. 1
FIG. 2

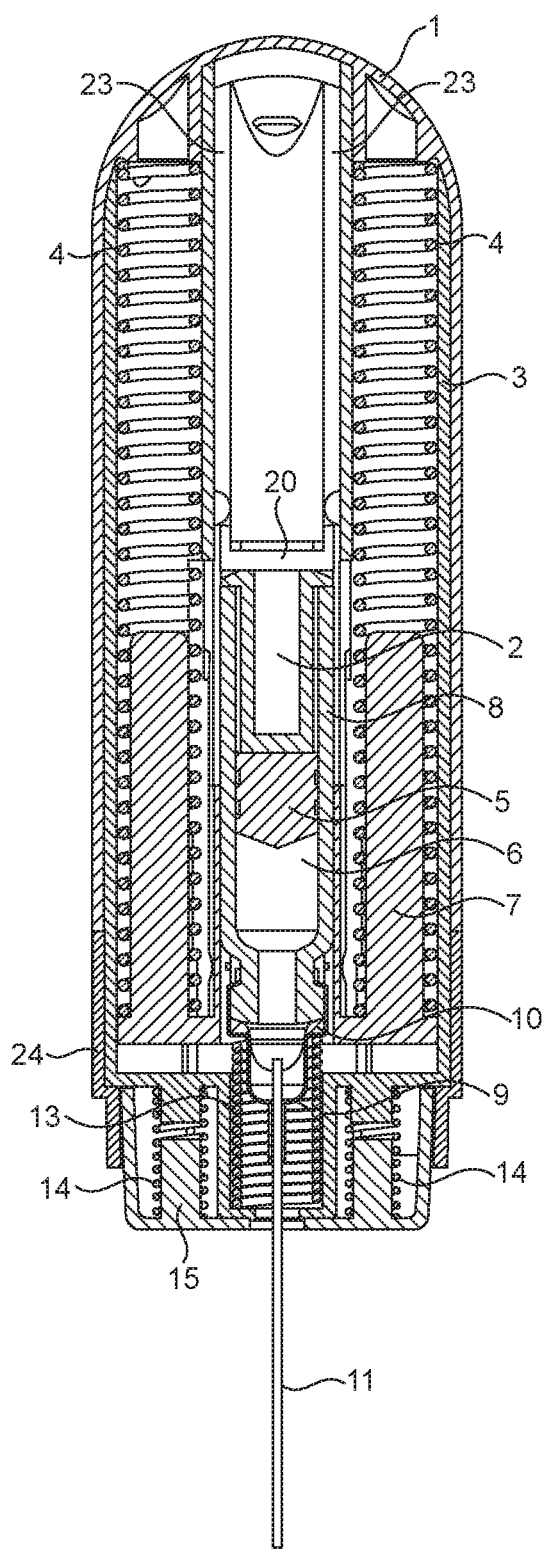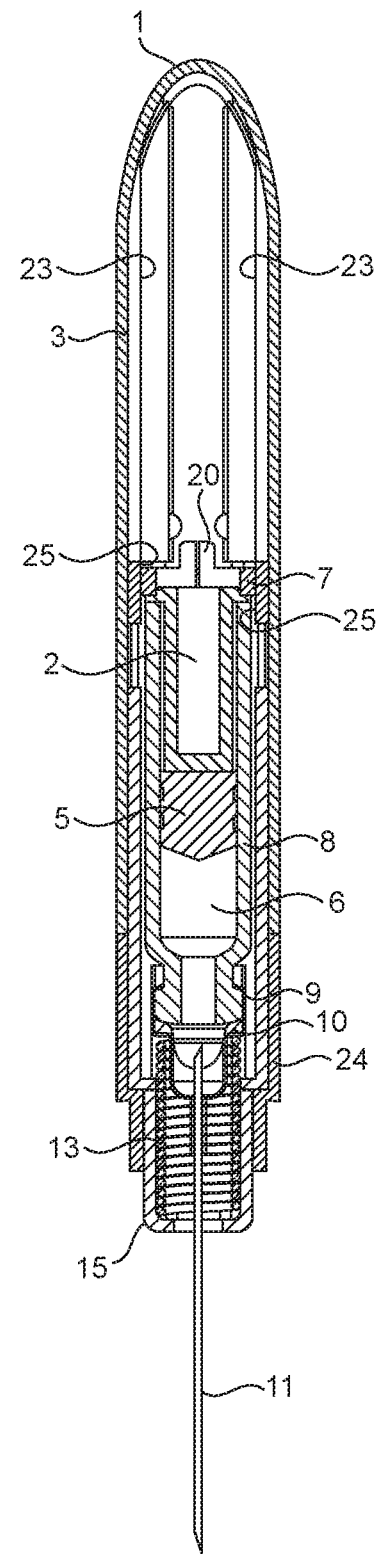
FIG. 14
FIG. 15

AUTOINJECTOR WITH RETRACTING NEEDLE

FIELD OF THE INVENTION

The invention relates needle safety mechanisms for injection devices.

BACKGROUND TO THE INVENTION

Needle-based drug delivery devices such as syringes and autoinjectors typically incorporate a needle safety mechanism to reduce the risk of accidental needle stick injuries after drug delivery.

Most of these mechanisms are 'passive' in that they deploy automatically, without the user needing to perform any extra actions to activate them after the drug has been delivered. Passive mechanisms have a clear advantage over 'active' systems (where the user needs to deploy the needle safety mechanism after drug delivery as a separate action) in that they ensure that the used needle is shielded.

These 'passive' mechanisms tend to fall into one of two types: 'retracting needle' type mechanisms and 'extending cover' type mechanisms.

Typically in retracting needle type mechanisms the needle is automatically withdrawn from the patient into the drug delivery device at a point dictated by the internal drug delivery mechanism. One issue that can occur with this approach is withdrawal of the needle before drug delivery is complete, resulting in drug not being delivered to the correct place in the patient. This is because it is difficult to create a delay between end of drug delivery and needle withdrawal without a complex 'lost motion' mechanism. Manufacturing tolerances prevent needle withdrawal at the exact point that drug delivery is completed. Any lost motion mechanism increases the size and complexity of the device.

A second issue with the retracting needle approach is that the drug can leak out of the hole left by the needle in the flesh of the patient if the needle is removed from the injection site too quickly. This is because the drug has not had sufficient time to be absorbed into the patient's body tissues, but still exists as a bolus within the patient's body. There is a therefore a potential benefit in maintaining the needle in position in the patient for a few seconds after the end of drug delivery to allow the body to accommodate the drug and reduce the risk of this issue.

In "extending cover" type mechanisms after drug delivery, the needle remains in the patient until the device, and hence the needle, is withdrawn from the patient, at which point a spring-loaded needle cover moves forwards relative to the needle and device body (as held by the user), and locks into place, shielding the needle. This approach allows the potential for the needle to remain in place in the patient until well after the completion of drug delivery, without the costs and complexity of a delayed withdrawal mechanism.

However, there is a specific disadvantage of this extending cover approach when longer needles are used in conjunction with small drug delivery devices, as the extending needle cover needs to be robust enough once extended to withstand handling and bending forces after deployment, so can compromise the small size of the device, and/or not be sufficiently robust.

Some devices, such as autoinjectors, benefit from being small in order to render them more portable and less frightening. In particular this impacts adrenaline autoinjectors, where there are published studies indicating that a significant cause of fatalities is lack of carriage of autoinjectors by users due to the size of the device. There is also evidence to suggest that the needle length used in the majority of current intramuscular autoinjectors is too short, and should be around 10 mm longer, at 25 mm inserted depth. There is therefore a need for smaller devices with longer needles.

The "extending cover" needle safety mechanisms have a greater impact on device size as the extended needle length to be covered becomes greater, because it has to extend further from the body of the main device whilst maintaining high levels of mechanical resistance to bend and break forces once deployed.

The object of the invention is to provide a needle safety mechanism suitable for small drug delivery devices with long needles, without the disadvantages of current retracting needle or extending cover mechanisms.

SUMMARY OF THE INVENTION

In a first aspect of the invention, there is provided an automatic drug delivery device comprising: a housing; a skin sensor element coupled to the housing and movable relative to the housing, wherein the skin sensor element is biased into a front position relative to the housing and is movable to a rear position relative to the housing when the skin sensor element is pressed against an injection site on a patient; a needle assembly comprising a hypodermic needle, the hypodermic needle extending outside of the housing when the device is in a needle insertion configuration; a drug delivery mechanism comprising a first stored energy source within the housing; and a needle retraction mechanism configured to withdraw the hypodermic needle into the housing when the needle retraction mechanism is released; wherein the needle retraction mechanism is coupled to the skin sensor element such that when the skin sensor element is moved from the rear position towards the front position, and the needle is in the needle insertion position, the needle retraction mechanism is released.

The device has a needle retracting mechanism which is activated by a skin sensor element rather than a drug delivery mechanism. This means that the needle is withdrawn into the body of the device when the device is moved away from the injection site by the user after the drug has been delivered. In this way, the timing of the needle safety mechanism is controlled by the user, not the drug delivery mechanism, but the user is not required to make an additional action in order to deploy the needle safety mechanism.

Preferably, the drug delivery mechanism is released when the skin sensor element is moved from the front position towards the rear position. Advantageously, the stored energy source is arranged to expand along an axis that is offset from an axis of travel of the needle assembly in use. The fact that the stored energy source is arranged to expand along an axis that is offset from an axis of travel of the needle assembly allows for a compact device to be realised. When a spring or springs are used as the stored energy source, this arrangement does not require to use of very large or powerful springs. The stored energy source may arranged to expand along an axis that is parallel with, or non-parallel with, an axis of travel of the needle assembly.

As used herein, front and proximal are used to mean the same end of the device, which is the end of the device through which drug is delivered to a patient. Similarly, rear and distal are used to mean the same end of the device, which is the end of the device opposite to the front end of the device. The term "injection site" as used here, means the area of a patient through which or to which a drug is to be delivered, such as a patient's thigh, torso or arm.

The drug delivery mechanism may be prevented from being released until the skin sensor element is moved from the front position to the rear position. Preferably, the drug delivery mechanism is released as a consequence of the skin sensor element being moved from the front position to the rear position. Alternatively, the movement of the skin sensor to the rear position may unlock a secondary release mechanism, such as a button.

In operation, the first stored energy source of the drug delivery mechanism may move the hypodermic needle from an initial position to an insertion position, and when the hypodermic needle is in the insertion position and the skin sensor element is moved from the rear position towards the front position, the hypodermic needle is uncoupled from the first stored energy source of the drug delivery mechanism. Alternatively, the first stored energy source of the drug delivery mechanism may move the hypodermic needle from an initial position to an insertion position, and when the hypodermic needle is in the insertion position and the skin sensor element is moved from the rear position towards the front position, the hypodermic needle may remain coupled to the first stored energy source but a second stored energy source may be released to overcome any force provided by the first stored energy source, to withdraw the needle into the housing.

The drug delivery mechanism may comprise a further stored energy source that, in operation, is released to deliver a drug through the hypodermic needle. Alternatively, the device may be configured so that the first stored energy source is used both to move the hypodermic needle from an initial position to an insertion position and to deliver the drug through the hypodermic needle.

The needle assembly preferably comprises a drug container containing a drug for injection. The hypodermic needle may be fixed to the drug container. The needle assembly may comprise a plunger rod. The drug delivery mechanism may be configured to move the needle and drug container to the insertion position and subsequently to move the plunger rod relative to the drug container to deliver the drug.

The drug delivery mechanism may comprise a drive member positioned between the first stored energy source and the needle assembly. The drive member may comprise a resilient portion that engages the needle assembly to drive the needle to a needle insertion position. The resilient portion may be moved out of engagement with the needle hub or drug container when the needle reaches the insertion position and the skin sensor element is moved from the front position to the rear position, so as to uncouple the first stored energy source from the needle assembly.

The drug delivery mechanism may prevent release of the needle retraction mechanism until the needle is in the needle insertion position. The drug delivery mechanism may prevent release of the needle retraction mechanism until at least some drug has been delivered through the hypodermic needle.

The skin sensor may be locked in the forward position after the needle retraction mechanism has been activated, to provide additional distance between the tip of the needle and the front of the skin sensor that covers it.

The first stored energy source may comprise one or more springs. Alternatively, the stored energy source may comprise a different resilient element or a compressed gas. The stored energy source may comprise an electrical energy store.

The needle retraction mechanism may comprise a second stored energy source configured to withdraw the hypodermic needle into the housing.

The second stored energy source may be restrained from retracting the needle by the first stored energy source. The first stored energy source may transfer energy to the second stored energy source as the needle is moved to the needle insertion position. In one embodiment, the second stored energy source is a spring, herein referred to as the needle safety spring. The needle safety spring may be compressed by the drug delivery mechanism as the needle is moved to the insertion position. When the hypodermic needle is in the insertion position and the skin sensor element is moved from the rear position towards the front position, the hypodermic needle may be uncoupled from the first stored energy source of the drug delivery mechanism. When the needle is uncoupled from the first stored energy source of the drug delivery mechanism, the needle safety spring can expand to retract the needle into the housing. As an alternative to a spring, the second stored energy source may be a gas that is compressed by the drug delivery mechanism as the needle is moved to the insertion position.

The needle safety spring can be held in a compressed condition by a retention feature prior to use of the device, so that it does not impact on the drug container before use, or cause the needle insertion or drug delivery force to be reduced. The needle safety spring can be uncoupled from the retention feature by travel of the skin sensor during use, or by the needle insertion or drug delivery mechanisms during use.

Alternatively, the first stored energy source of the drug delivery mechanism may move the hypodermic needle from an initial position to an insertion position, and when the hypodermic needle is in the insertion position and the skin sensor element is moved from the rear position towards the front position, the hypodermic needle may remain coupled to the first stored energy source but a second stored energy source may be released to overcome any force provided by the first stored energy source, to withdraw the needle into the housing. In one embodiment the second stored energy source is a needle safety spring that is locked in a compressed state until the skin sensor is moved from the rear position towards the front position, and the needle is in the needle insertion position. When the needle safety spring is released it expands and overcomes the force provided by the first stored energy source, to withdraw the needle into the housing. The first stored energy source may be a spring or springs with a smaller spring constant than the needle safety spring.

The drug delivery mechanism may be prevented from being released until the skin sensor element is moved from the front position to the rear position. Preferably, the drug delivery mechanism is released as a consequence of the skin sensor element being moved from the front position to the rear position. The drug delivery mechanism may be restrained from release by a coupling between the drug delivery mechanism and the housing. This coupling may be released when the skin sensor is in the rear position. The drive member of the drug delivery mechanism may be restrained relative to a portion of the housing by a locking member engaging a portion of the drive member. The locking member may be part of the housing or may be a separate element. The locking member may be restrained from moving out of engagement with the drive member by the skin sensor until the skin sensor is moved to the rear position. In the rear position an aperture in the skin sensor or a discontinuation of a locking surface on the skin sensor, may align with the locking member, allowing the locking member to move out of the engagement with the drive member.

In one embodiment, the locking member comprises a plurality of balls. The balls are each engaged with a recess in the drive member and in an aperture in an inner portion of the housing to restrain the drug delivery mechanism from moving relative to the housing. The skin sensor prevents the balls from moving out of the recess in the drive member until it is in the rear position. When the skin sensor is in the rear position, the first stored energy source urges the balls out of the recess and into an opening in the skin sensor. As an alternative, the locking member may comprise a plurality of latches on the housing that each engage a corresponding latch or recess on the drive member. The latches may be provided on resilient limbs that are prevented from flexing to disengage the latches from the drive member by the skin sensor. Only when the skin sensor is in the rear position are the latches able to disengage from the drive member.

The skin sensor may comprise a plurality of locking surfaces. The skin sensor may comprise a plurality of apertures. The skin sensor may be biased into a forward position relative to the housing by one or more skin sensor springs.

The drive member may comprise a resilient portion that deforms to disengage from the needle assembly when the needle assembly is in the insertion position and the skin sensor is moved out of the rear position. In one embodiment, the drive member comprises a spring seat and an engagement portion configured to engage the needle assembly, wherein the spring seat and the engagement portion are connected by the resilient portion. The resilient portion may comprise one or more resilient arms. The drive member may comprise a plurality of spring seats and plurality of engagement portions, each spring seat connected to an engagement portion by one or more resilient arms. The engagement portions may engage a needle hub or the drug container. Alternatively, when the first stored energy source is also used to deliver the drug, the engagement portions may engage a plunger rod. The plunger rod may be configured to move in the drug container to deliver the drug through the hypodermic needle.

The resilient arms may be configured to flex in a direction orthogonal to a direction of travel of the needle assembly from an initial position to the needle insertion position. The resilient arms may be held in tension by the first stored energy source as the needle assembly moves to the needle insertion position.

The drive member may comprise at least two resilient arms extending on opposite sides of needle assembly and at least one spring seat connected to the resilient arms and engaging the stored energy source of the drug delivery mechanism. In one embodiment, the drive member comprises two pairs of resilient arms, the resilient arms in each pair of resilient arms coupled together by an engagement portion that engages a rear end of a plunger rod.

The needle assembly may comprise a cam surface that engages the drive member to ensure disengagement of the needle assembly from the drive member when the one or more resilient arms is allowed to flex. The cam surface may be provided on a needle hub, the drug container or on the plunger rod. A cam surface may be provided to engage with each of the engagement portions of the drive member.

Alternatively, or in addition, cam surface may be provided on each of the engagement portions of the drive member.

Each of the cam surfaces on the needle assembly may abut an engagement portion of the drive member at an angle oblique to the direction of travel of the needle assembly relative to the housing, so that when the one or more resilient arms is allowed to flex, the action of the first stored energy source or the second stored energy source, or both the first stored energy source and the second stored energy source, forces the needle assembly to disengage from the drive member.

The first stored energy source may be arranged within the housing so that the needle travels through or past at least a portion of the first stored energy source as it is withdrawn into the housing. This allows for a compact device. In one embodiment the first stored energy source comprises first and second drive springs arranged on opposite sides of the needle assembly when the needle is in a retracted position. The second stored energy source may be a spring arranged to expand in a space between the drive springs.

The drug delivery device may be an autoinjector. The autoinjector may be configured to be manually held in operation.

The device may comprise a drug for delivery to a patient. The drug may be a liquid. In one embodiment the drug is epinephrine.

The needle may have an extended length, i.e. the length of the needle that extends into the injection site, of between 5 mm and 50 mm, and preferably between 10 mm and 25 mm.

BRIEF DESCRIPTION OF THE DRAWINGS

Embodiments of the invention will now be described in detail, by way of example only, with reference to the accompanying drawings in which:

FIG. 1 is a schematic cross-sectional illustration of a drug delivery device in accordance with a first embodiment of the invention, before use;

FIG. 2 is an alternative cross-sectional view of the device of FIG. 1;

FIG. 14 is a cross-sectional view of the device of FIG. 13 after the drug seal has ruptured, opening a fluid path between the drug and the needle;

FIG. 15 is an alternative cross-sectional view of the device of FIG. 14;

FIG. 19b is a detail view of FIG. 19a;

DETAILED DESCRIPTION

Figure 3:
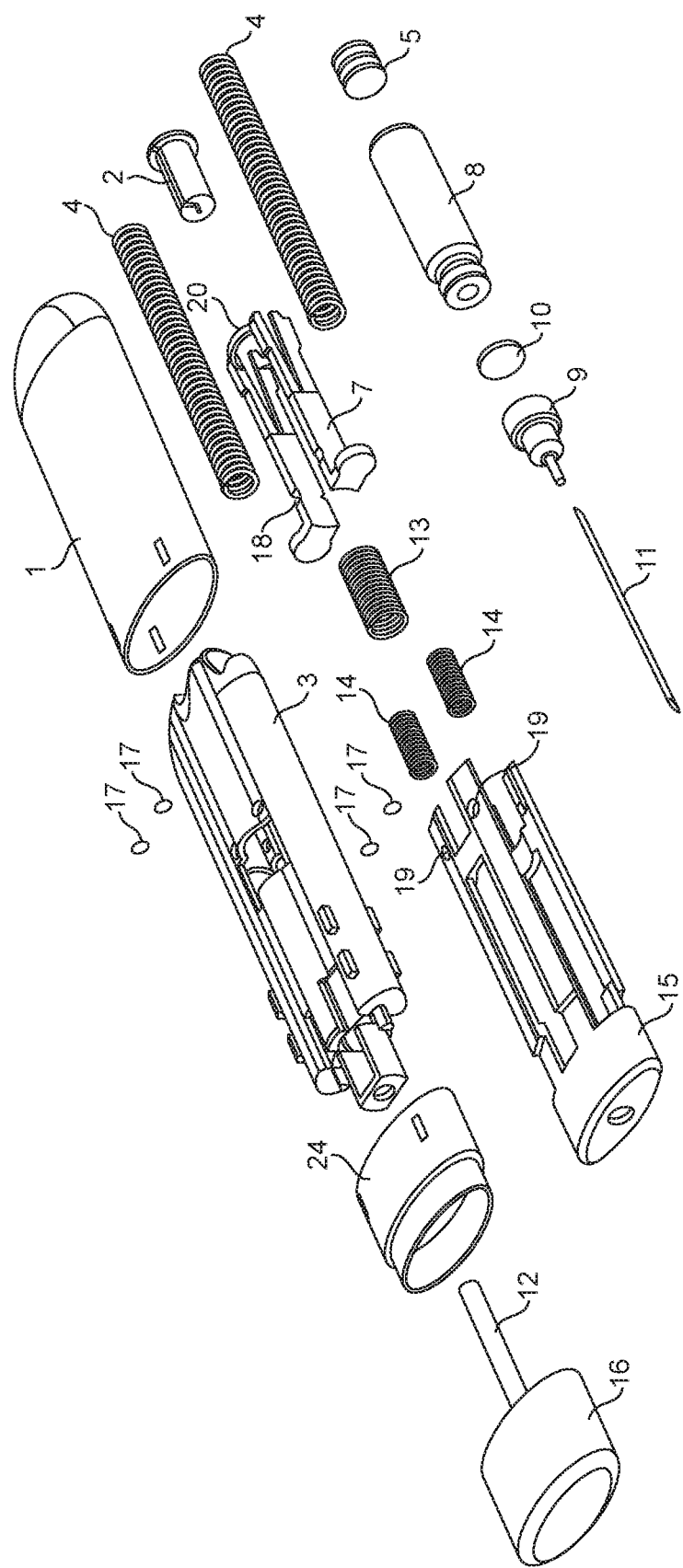
FIG. 3 is an exploded view of the device of FIGS. 1 and 2.

FIG. 1 shows a section view of an example of an autoinjector in accordance with the present invention. FIG. 2 is an alternative section view of the autoinjector of FIG. 1. FIG. 3 is an exploded view of the autoinjector of FIG. 1

The autoinjector comprises a cartridge 8 that contains a drug 6. The cartridge is attached to a needle hub 9. A needle 11 is fixed to the hub 9. The cartridge 8 is sealed from the needle 11 by a drug seal 10. The other end of the cartridge 8 is closed by a plunger 5.

The autoinjector has an external housing having an upper housing 1 and a lower housing 24. The external housing contains the cartridge 8. In use, the cartridge is moved relative to the external housing to insert the needle 11 into an injection site, as will be described. Two main drive springs 4 are provided to drive the cartridge forward to insert the needle into the injection site and subsequently to move the plunger 5 within the cartridge to eject the drug 6. The main drive springs 4 are positioned between the external housing 1 and a yoke 7. Before use of the autoinjector the main drive springs are in a compressed condition, as shown in FIG. 1. They are held in a compressed condition before use because the yoke is restrained from moving relative to the external housing. A back portion of the yoke 20 bears on a plunger rod 2. The plunger rod 2 bears on the plunger 5.

An inner housing 3 is fixed to both the upper external housing 1 and the lower external housing 24.

A skin sensor 15 is provided at a front end of the autoinjector and is slidable coupled to the inner housing 3, and extends within the external housing 1. The skin sensor 15 is urged forwards by two skin sensor springs 14 mounted between the skin sensor and the inner housing 3, but retained on the inner housing 3 by engagement of skin sensor bracing arms 26 with a recess on the inner housing.

A needle safety spring 13 is provided between the needle hub 9 and a front end of the inner housing 3. The needle safety spring is much weaker than the main drive springs and is initially in an uncompressed condition.

A cap 16 is coupled to the external housing 1 and covers the front of the autoinjector. The cap includes a needle shield portion 12 that is positioned within the needle safety spring.

The autoinjector also includes a locking mechanism that prevents release of the drive springs 4. The components of this mechanism can be seen in FIG. 3. Four locking balls 17 are retained in corresponding recesses 18 in the yoke 7 and holes 28 in the inner housing 3, preventing relative movement between the yoke and the inner housing.

Figure 4:
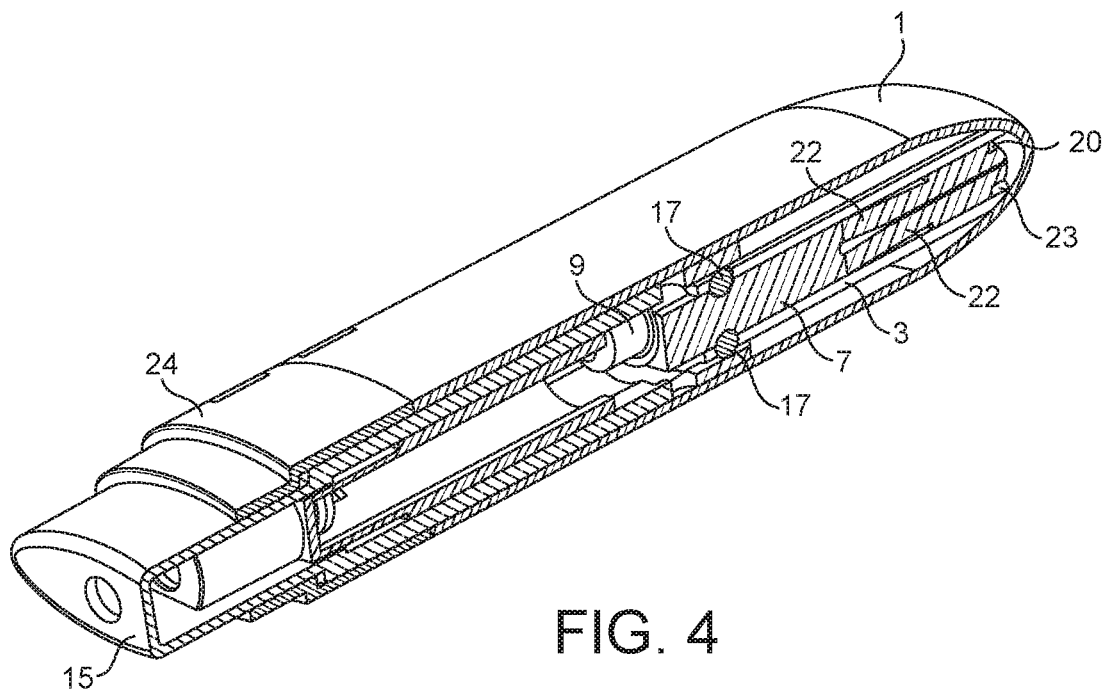
FIG. 4 is a further cross-sectional view of the device of FIG. 1, illustrating the locking mechanism restraining the main drive springs, with the cap removed.

FIG. 4 is a section view of the autoinjector of FIG. 1 with the cap 16 removed, showing the locking balls 17. The locking balls 17 prevent the yoke 7 from being moved forward by the main drive springs 4, by locking the yoke 7 to the inner housing 3. The locking balls 17 are retained in position by the skin sensor 15.

Figure 5:
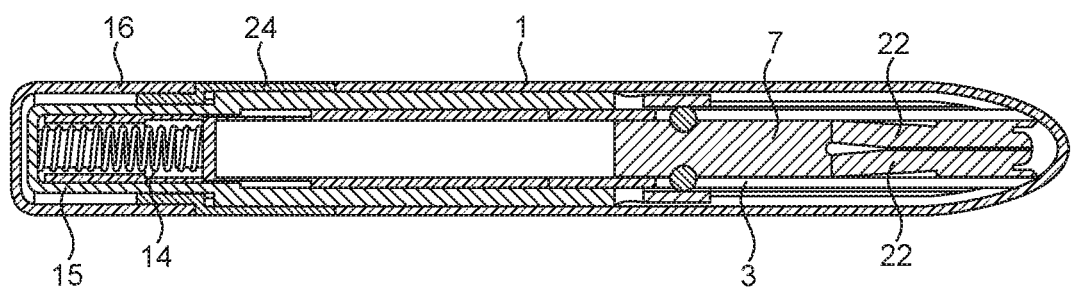
FIG. 5 is a still further cross-sectional view of the device of FIG. 1 illustrating the locking mechanism restraining the main drive springs.

FIG. 5 is an alternative section view of the autoinjector of FIG. 4, showing the cap in place.

The various components shown in FIG. 3 may be moulded or otherwise formed from plastics materials and metals or other materials commonly used in drug delivery devices.

The operation of the autoinjector shown in FIGS. 1 to 5 will now be described.

Figure 6:
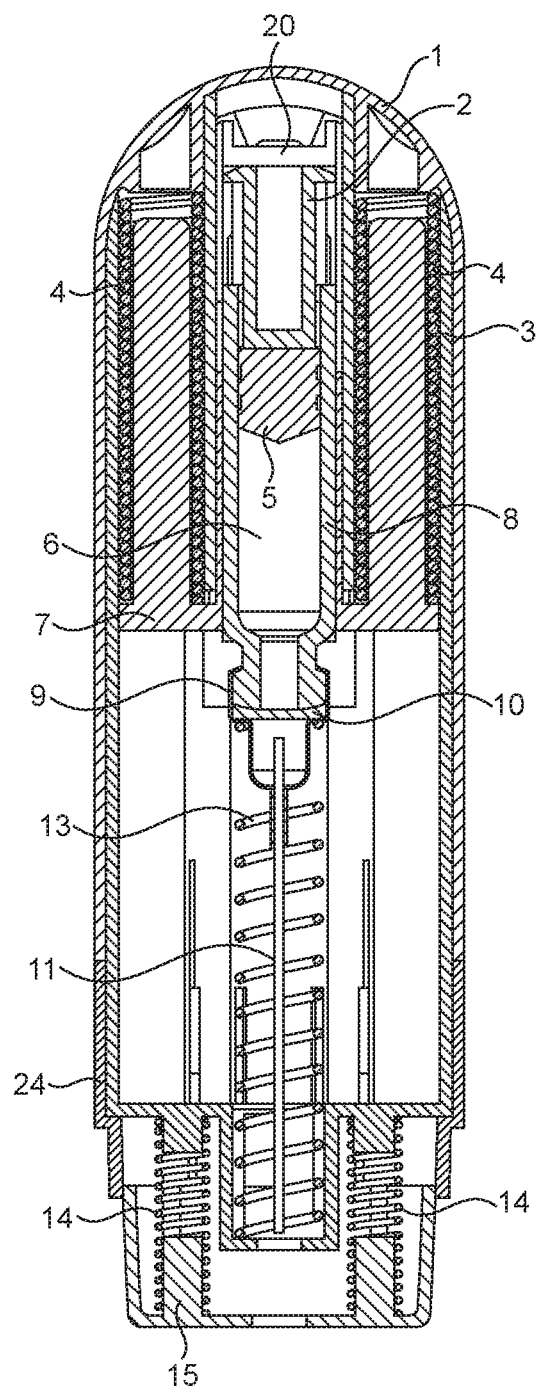
FIG. 6 shows the device of FIG. 1 with the cap removed.

FIG. 6 is a section view of the autoinjector of FIG. 1 with the cap removed, ready to use.

Figure 7:
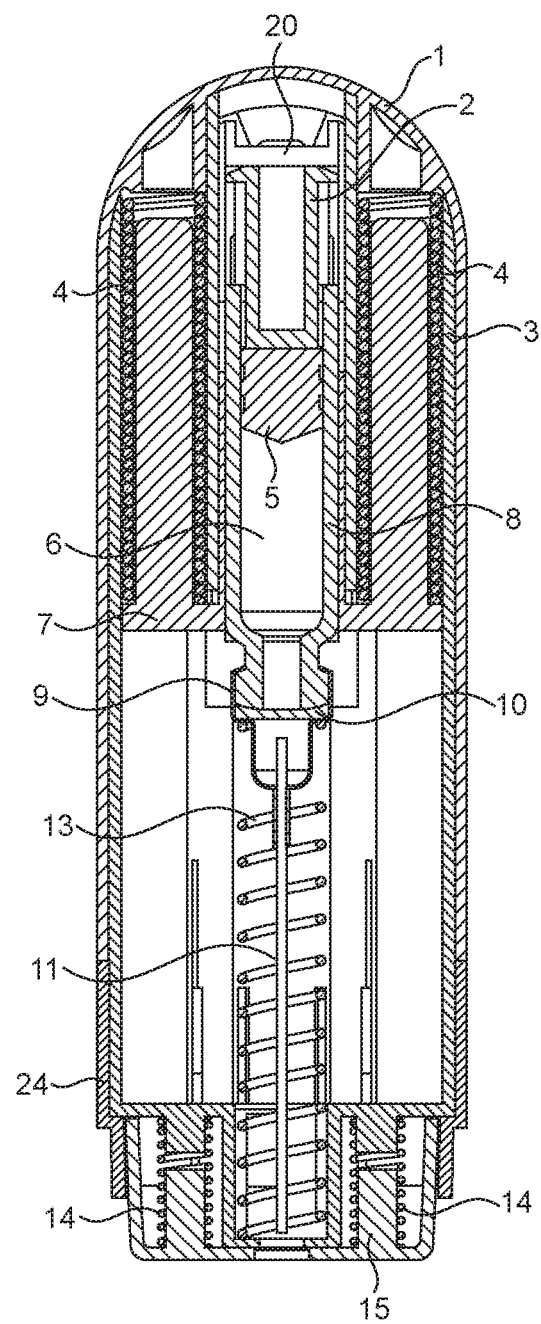
FIG. 7 is a cross-sectional view of the device of FIG. 6, with the skin sensor moved to the 'activated' position.

To activate the autoinjector, the skin sensor 15 is pressed against an injection site on a patient. FIG. 7 is a section view of the autoinjector of FIG. 6 with the skin sensor 15 moved backwards, compressing the biasing springs 14.

Figure 8:
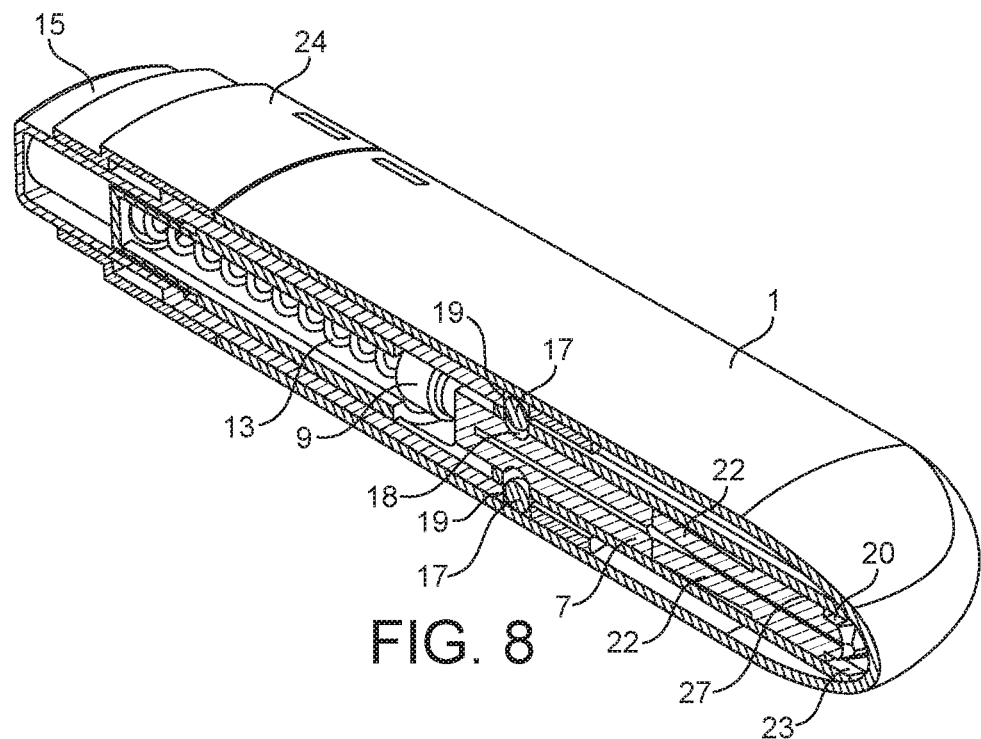
FIG. 8 is an alternative cross-sectional view of the device of FIG. 7 showing the locking mechanism in the unlocked position.
Figure 8A:
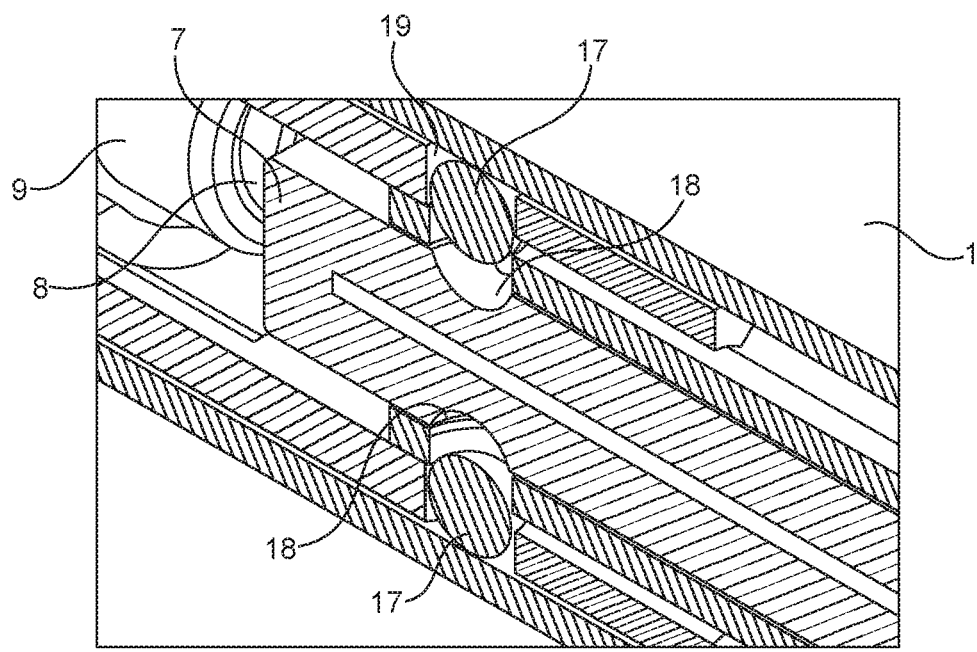
FIG. 8A is a detailed view of FIG. 8.

FIG. 8 is a section view of the autoinjector of FIG. 7, showing the locking balls 17 moving out of the locked position in the recesses 18 in the yoke 7, into an unlocked position that allows the yoke to move relative to the inner housing. This is possible because holes 19 in the skin sensor 15 have lined up with the locking balls 17 as the skin sensor 15 has been moved backwards. FIG. 8a is a detail view of FIG. 8 showing the holes 19 more clearly.

When the locking balls are moved out of the recesses 18 on the yoke, the yoke is driven forwards relative to the inner housing 3 by the main drive springs 4. It main drive springs 4 are positioned on opposite sides of the cartridge 8. It can be seen that the drive springs 4 expand along an axis offset from the axis of the needle. The back of the yoke 20 has thrust arms 22 that engage the plunger rod 2 and so moves the plunger rod 2 forwards, and with it the cartridge, needle and hub. The drug seal 10 prevents plunger moving within the cartridge and the drug 6 from being dispensed through the needle 11 at this stage.

Figure 9:
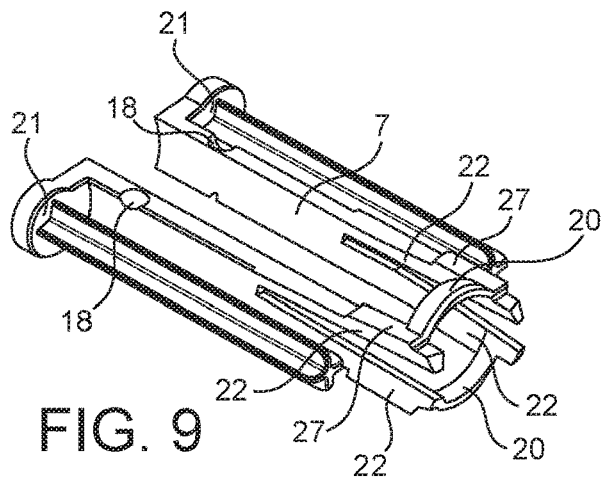
FIG. 9 is a perspective view of the yoke component.

FIG. 9 is a perspective view of the yoke 7 component. It has two thrust faces 21 to take the load from the two main drive springs 4, and two further thrust arms 22 that apply this load to the plunger rod 2, and which form part of the back 20 of the yoke 7. Before and during drug delivery, these thrust arms 22 are held closed by bearing surfaces 27 bearing on corresponding bearing surfaces 23 on the inner housing 3, as shown in FIG. 8.

Figure 10:
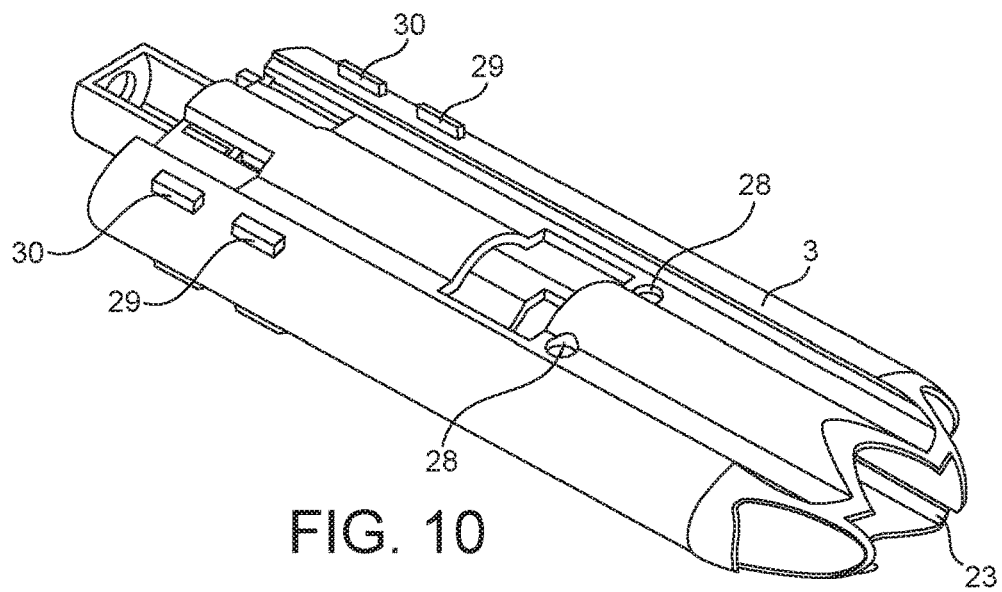
FIG. 10 is a perspective view of the inner housing.
Figure 11:
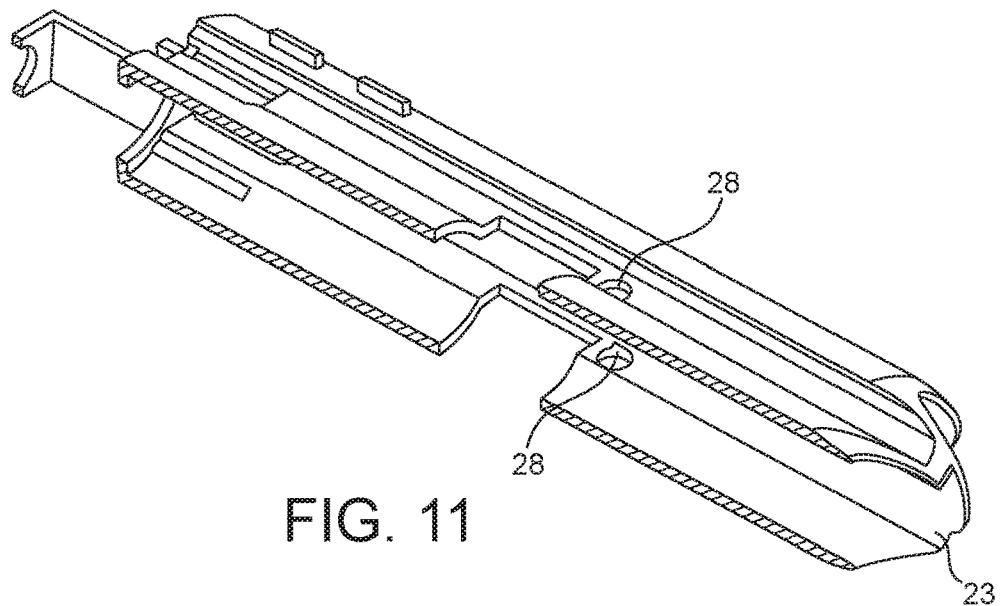
FIG. 11 is a cross-sectional perspective view of the inner housing.

FIG. 10 is a perspective view of the inner housing 3. The bearing surfaces 23 of the inner case 3 retain the yoke thrust arms 22, as described. The holes 28 work in combination with the locking balls 17 to lock the yoke 7 in position until the autoinjector is activated. Protrusions 29 are used to lock the inner housing to the upper external housing 1. Protrusions 30 are used to lock the inner housing to lower external housing 24. FIG. 11 is a section view of the inner case 3 of FIG. 10.

Figure 12:
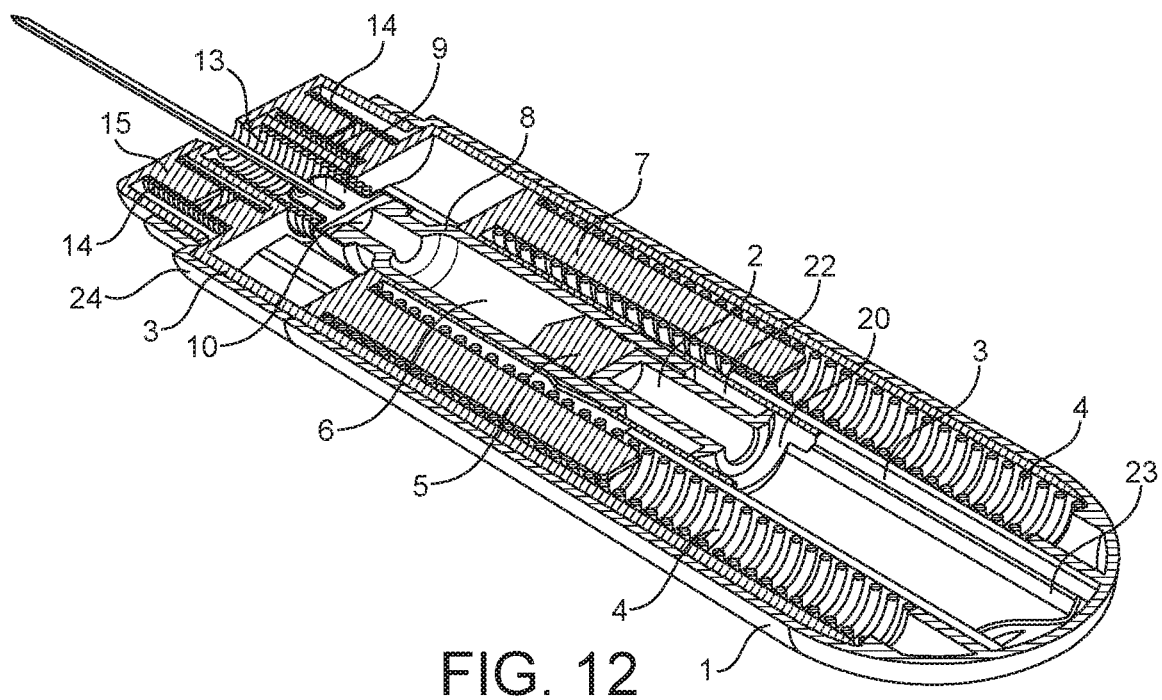
FIG. 12 is a cross-sectional view of the device of FIG. 8 after the needle has moved to the 'inserted' position

FIG. 12 shows a section view of the autoinjector of FIG. 1 after the needle 11 has been inserted into the patient. The needle safety spring 13 has been compressed by the main drive springs 4 acting on the back 20 of the yoke 7, which in turn moves the plunger rod 2 forwards, and with it the cartridge, needle and hub. As described, the drug seal 10 prevents the drug 6 from being dispensed through the needle 11 at this stage.

Figure 13:
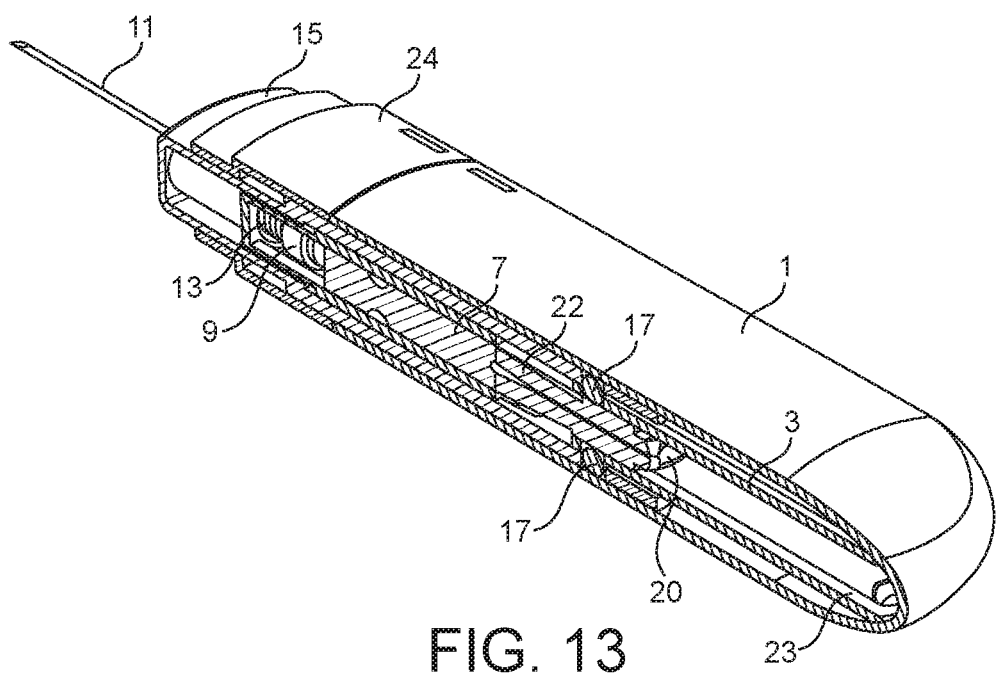
FIG. 13 is an alternative cross-sectional view of the device of FIG. 12 showing the drive spring retention mechanism in the unlocked position.

FIG. 13 is an alternative section view of the autoinjector of FIG. 12.

Once the cartridge reaches the forward position shown in FIGS. 12 and 13, it cannot move any further forwards. The pressure exerted by the main drive springs 4 on the plunger 5 through the yoke and plunger rod then causes the drug seal 10 to deform and rupture on a back end of the needle 11. Once the drug seal 10 has been ruptured, the drug can be delivered to the injection site through the needle. The plunger rod moves relative to the cartridge to dispense the drug until a rear lip on the plunger rod abuts a rear end of the cartridge 8.

FIG. 14 is a section view of the autoinjector of FIG. 1 after the drug 6 has been dispensed. The cartridge 8 has moved fully forwards and the pressure on the drug 6 due to the main drive springs 4 acting on the back 20 of the yoke 7 has caused the drug seal 10 to stretch and be pierced by the back end of the needle 11, allowing the drug 6 to be dispensed through the needle 11 into the patient.

FIG. 15 is an alternative section view of the autoinjector of FIG. 14. It can be seen that with the cartridge in the fully forward position, the yoke bearing surfaces 27 are no longer supported by inner case bearing surfaces 23, but are supported by the skin sensor bearing surfaces 25.

Following delivery of the drug, the autoinjector is removed from the injection site. The autoinjector is constructed so that when the skin sensor 15 is moved forwards again by the skin sensor springs 14 as the autoinjector is removed from the injection site, the needle 11 is retracted back into the inner housing 3

Figure 16A:
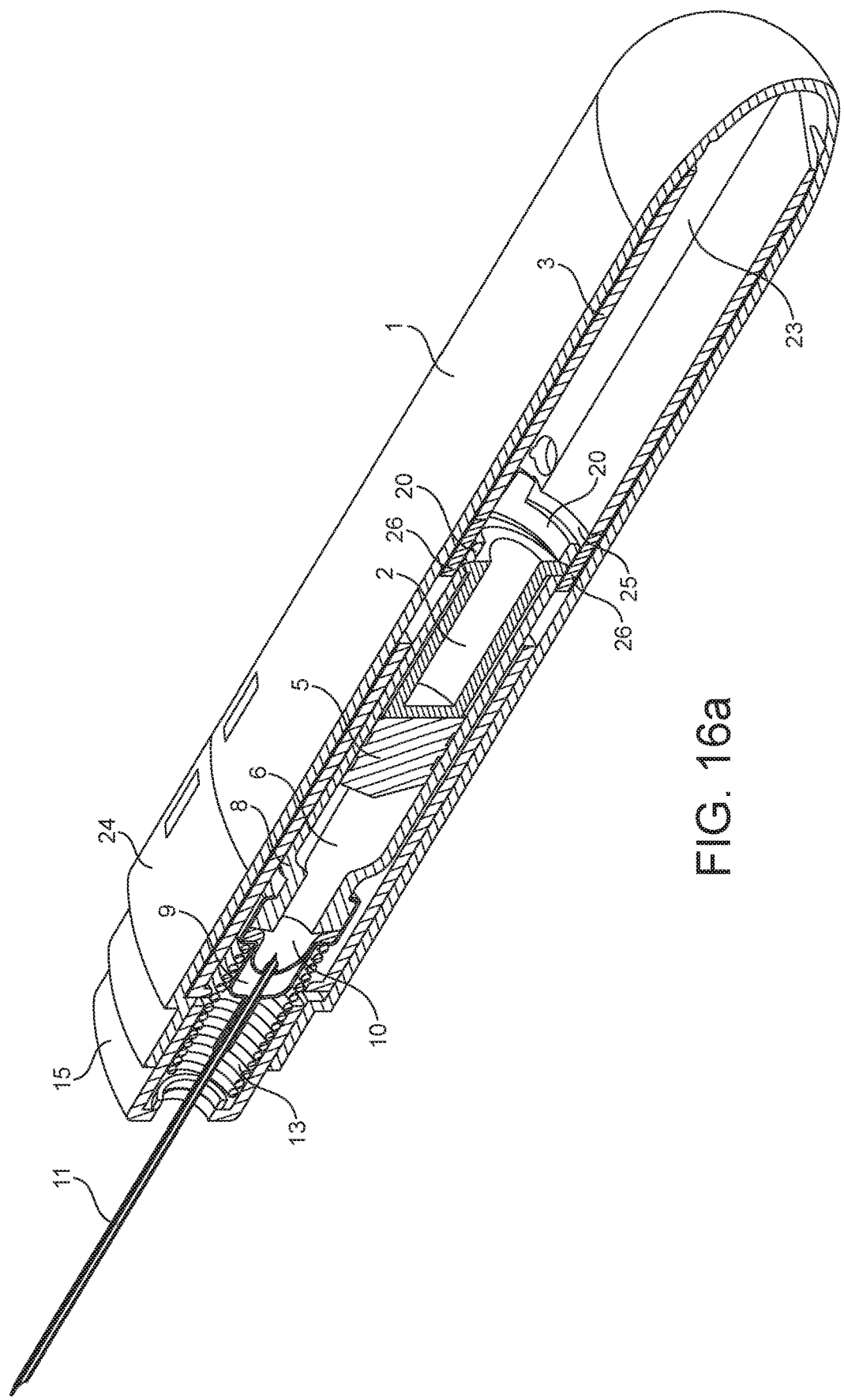
FIG. 16a is an alternative section view of the autoinjector of FIG. 14.
Figure 16B:
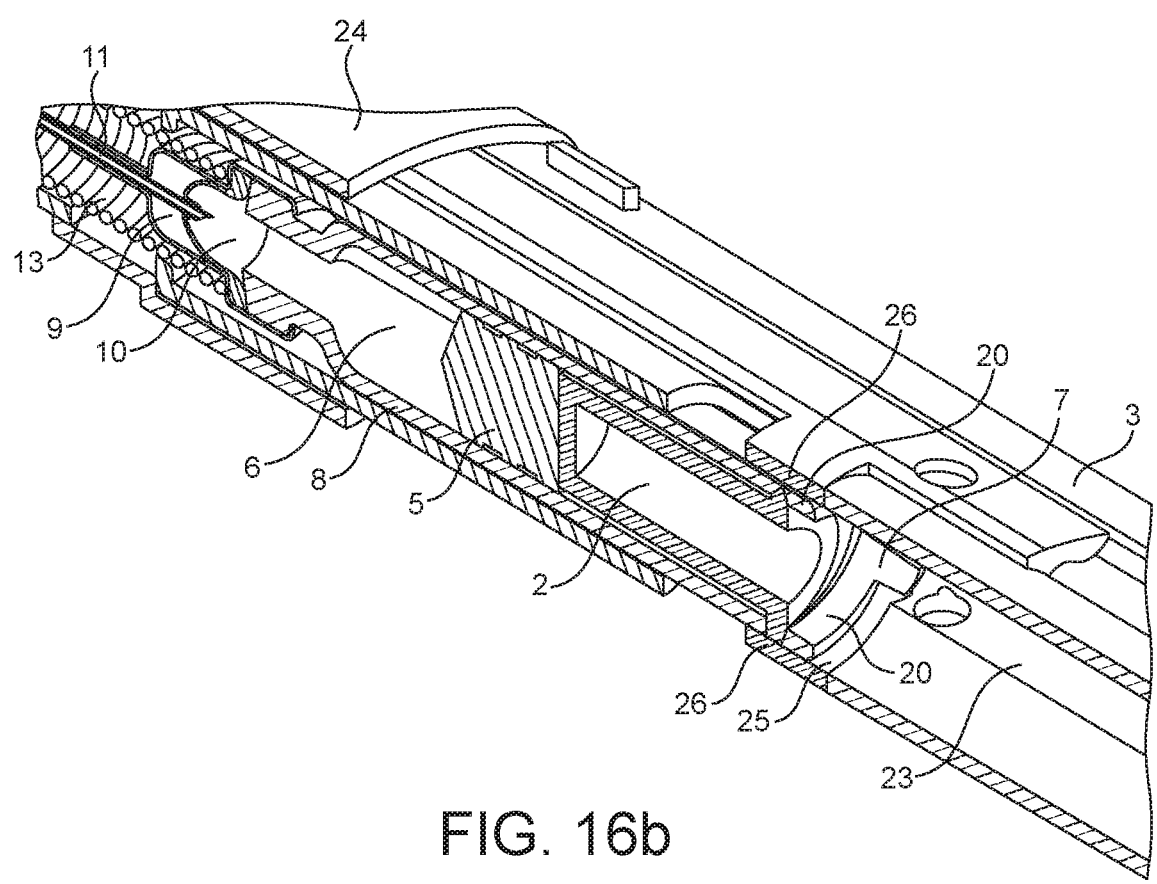
FIG. 16b shows a detail of FIG. 16a, with the outer case hidden for clarity.

FIG. 16a is an alternative section view of the autoinjector of FIG. 14. FIG. 16b shows a detail of FIG. 16a, with the outer case hidden for clarity. The skin sensor bracing arms 26 constrain the yoke thrust arms 22 so that they continue to bear on the plunger rod 2 even though they are no longer held in place by the inner body bearing surfaces 23. This is because the back of the yoke 20 is in contact with the skin sensor bearing surfaces 25. The outer case 1 (not shown) supports the skin sensor bracing arms 26.

Figure 17:
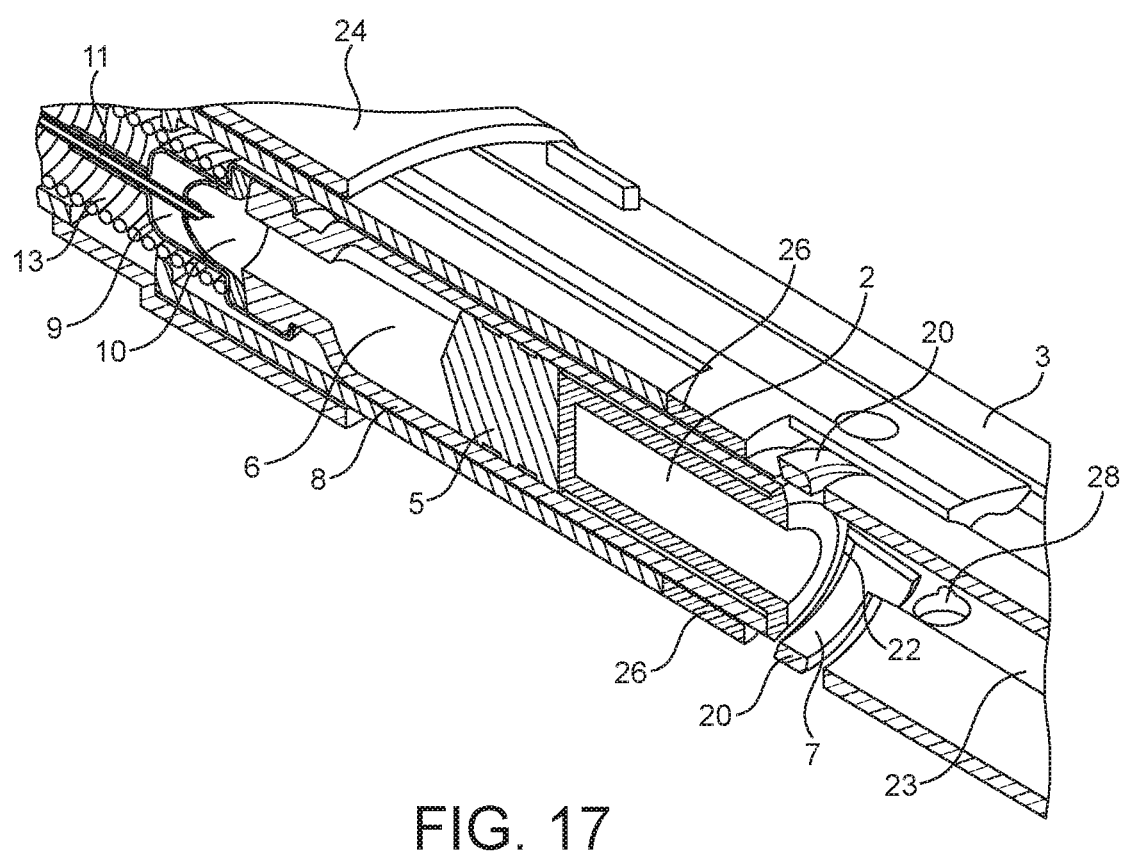
FIG. 17 shows a similar detail section view of the autoinjector to FIG. 16b, with the outer case hidden for clarity, at a point after the skin sensor has been allowed to move forwards.

FIG. 17 shows a similar detail section view of the autoinjector to FIG. 16b, with the outer case hidden for clarity, at a point after the skin sensor 15 has been allowed to move forwards by the skin sensor springs 14 due to the autoinjector being pulled away from the injection surface of the patient following drug delivery. It can be seen that the skin sensor bracing arms 26 have moved forwards with the rest of the skin sensor, allowing the yoke thrust arms 22 to move apart, releasing the plunger rod 2 from engagement with the yoke and main drive springs 4. With the cartridge no longer engaged with the main drive springs, the needle safety spring urges the needle hub 9, and with it the needle 11, cartridge 8 and plunger rod 2, rearwards within the inner housing 3.

Figure 18:
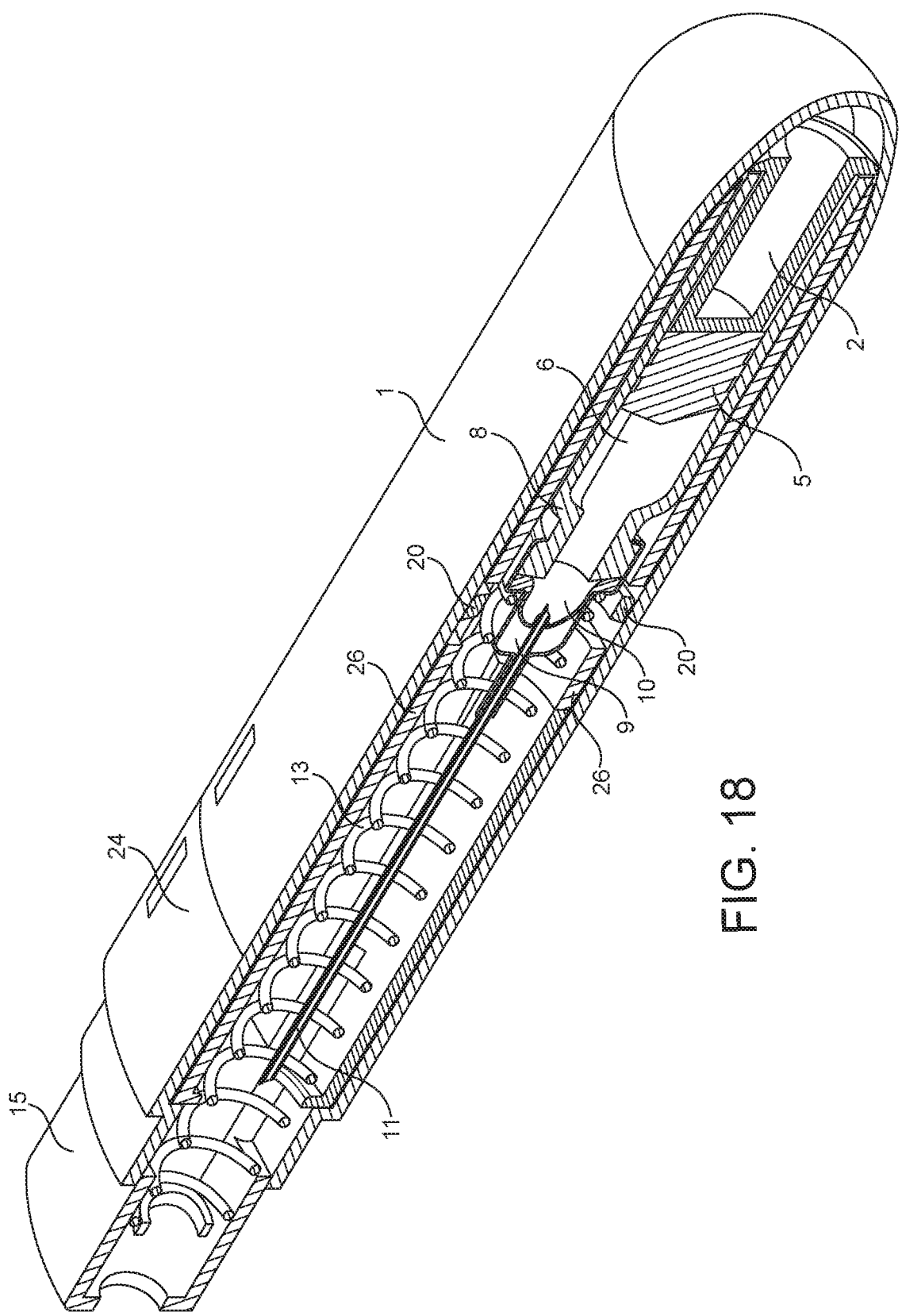
FIG. 18 shows a section view of the autoinjector after the cartridge, needle and plunger rod have been pushed back by the needle safety spring.

FIG. 18 shows a section view of the autoinjector after the cartridge 8, needle 11 and plunger rod 2 have been pushed back by the needle safety spring 13, having been released from the main drive springs due to the movement of the yoke thrust arms 22. The needle is moved back past the main drive springs 4 until the plunger rod 2 abuts the external housing 1. In this position the needle 11 is retracted inside the external housing.

Figure 19A:
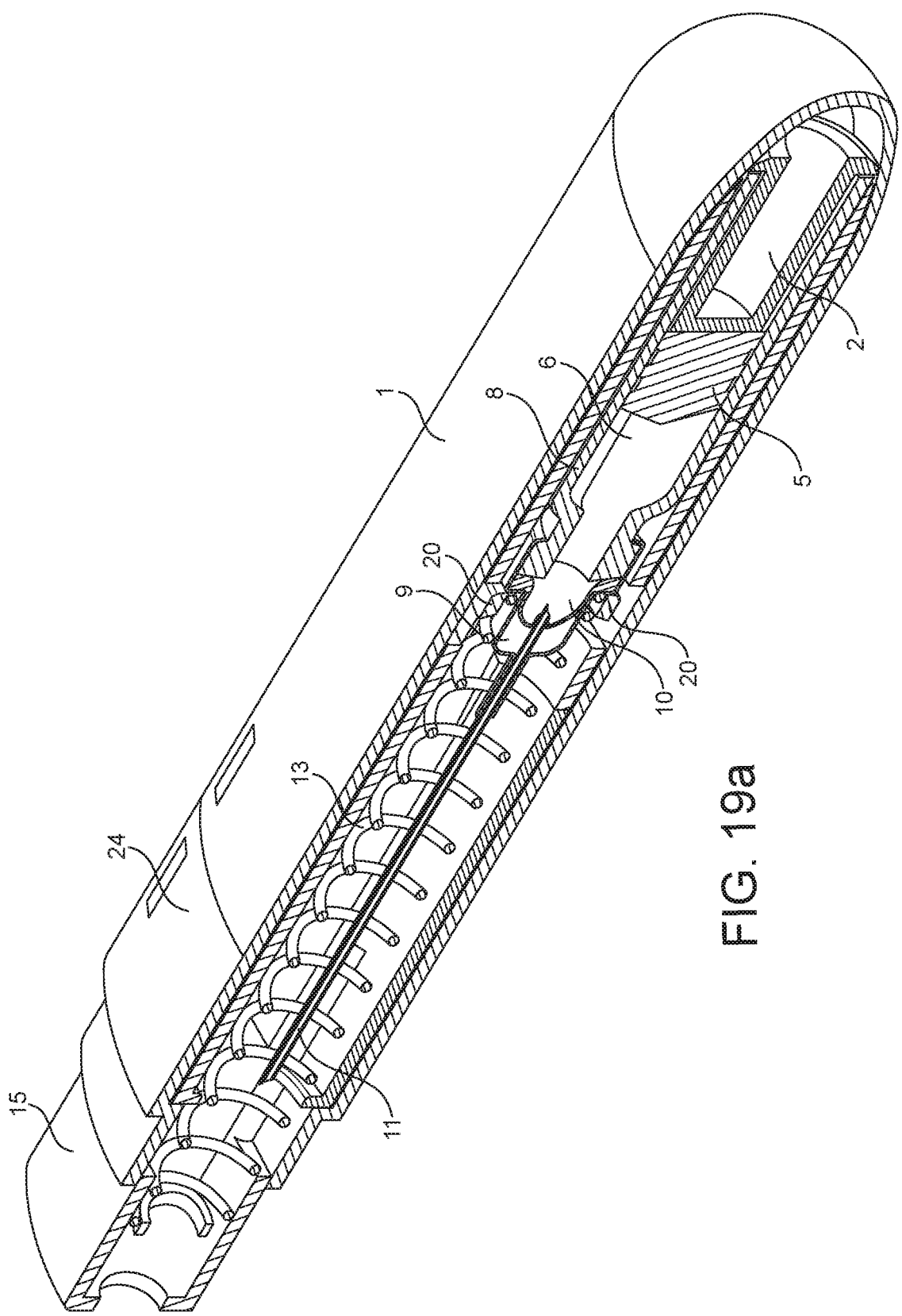
FIG. 19a is a section view of the autoinjector of FIG. 1 after use, with the needle retracted back inside the body.
Figure 19B:
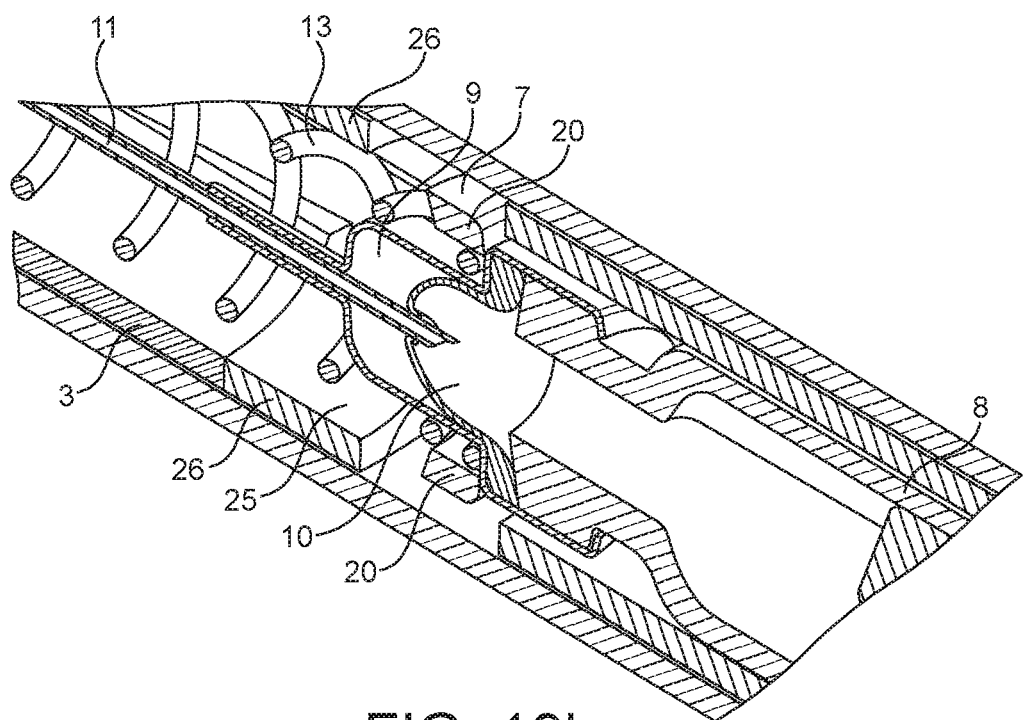

FIG. 19a is a section view of the autoinjector of FIG. 1 after use, with the needle retracted back inside the body. The yoke arms 22 have sprung back to their original position due to the resilience of the yoke material, causing the back of the yoke 20 to block forward movement of the cartridge 8 and needle 11. This prevents the risk of a needle stick injury due to the needle moving forwards against the needle safety spring 13, for instance due to inertia during handling of a used autoinjector. FIG. 19b is a detail view of FIG. 19a.

The embodiment described above has main drive springs that expand along axes offset from but parallel to the axis of movement of the needle assembly during operation. However it is possible for the drive spring or springs, or other stored energy source, to expand along an axis non-parallel to the direction of travel of the needle. FIGS. 20a-20e are a schematic illustration of such a device.

Figure 20A:
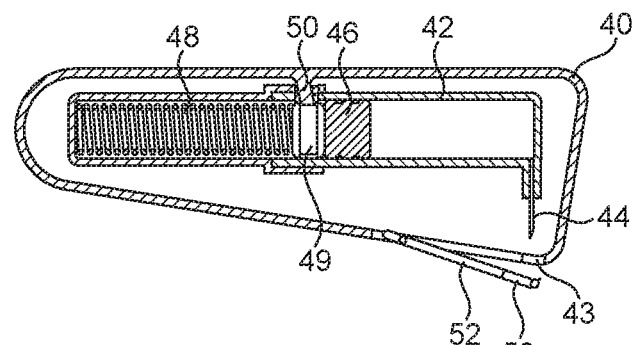
FIG. 20a is a schematic illustration of an alternative embodiment in accordance with the invention, prior to use.

FIG. 20a is an illustration of an alternative embodiment in accordance with the invention, prior to use. The device shown in FIG. 20 is an autoinjector comprising a housing 40 containing a cartridge 42 containing a drug to be delivered. A hypodermic needle 44 is fixed to the cartridge. A rear end of the cartridge is closed by a plunger 46. A drive spring 48 is positioned to drive the plunger 46 through the cartridge 42 to eject the drug through the needle 44. Prior to use, the drive spring is restrained from acting on the plunger 46 by the engagement of a protrusion 50 on the housing with a drive element 49 positioned between the drive spring and the plunger. A skin sensor element 52 is pivotally connected to the housing 40. The skin sensor element 52 has an aperture 53, which aligns with an aperture 43 on the housing, through which the needle can pass in use, as will be described.

Figure 20B:
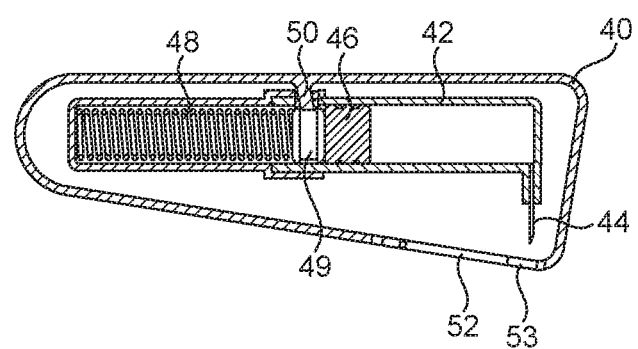
FIG. 20b shows the embodiment of FIG. 20a with the skin sensor retracted.
Figure 20C:
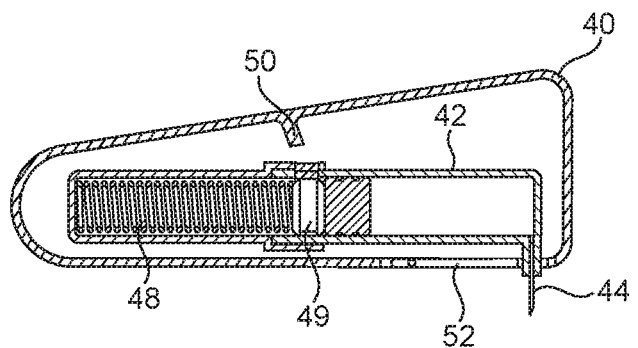
FIG. 20c shows the embodiment of FIG. 20b with the needle in an insertion position.

FIG. 20b shows the device of FIG. 20a with the skin sensor element 52 pushed back against the housing 40 when it has been placed on an injection site. FIG. 20c shows the device of FIG. 20b with the needle subsequently moved to a needle insertion position. The cartridge and drive mechanism are pivoted within the housing so that the needle extends through apertures 43 and 53 and into the injection site. A needle insertion mechanism (not shown) may be used to drive the needle to the needle insertion position shown in FIG. 20c. The needle insertion mechanism may be released by the movement of the skin sensor or by other means, such as a user actuated button. Alternatively the needle insertion may be effected manually.

Figure 20D:
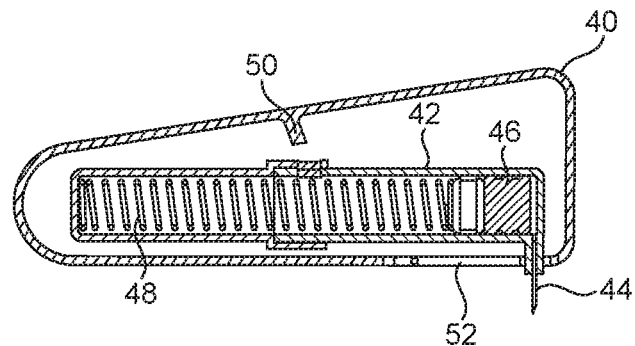
FIG. 20d shows the embodiment of FIG. 20c after the drug has been delivered.

Movement of the cartridge to the needle insertion position releases the protrusion 50 from the drive element 49. This releases the drive spring 48 to push the plunger 46 through the housing to eject the drug through the needle and into the injection site. FIG. 20d shows the device of FIG. 20c after the drug has been ejected.

Figure 20E:
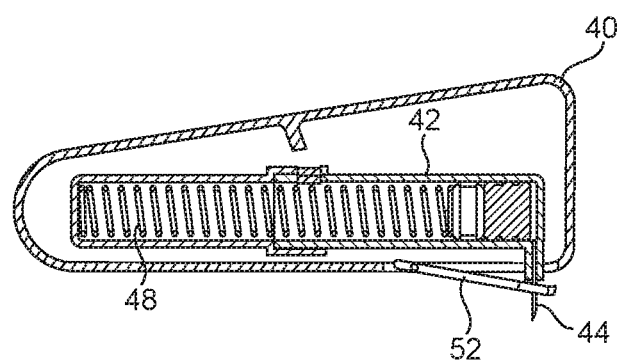
FIG. 20e shows the embodiment of FIG. 20d after withdrawal of the skin sensor from the injection site.
Figure 20F:
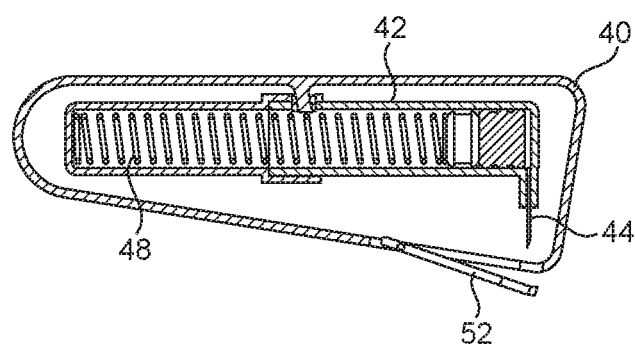
FIG. 20f shows the embodiment of FIG. 20e with the needle retracted.

Following drug ejection, the device is lifted from the injection site. The skin sensor element 52 is then pushed away from the injection site by a biasing spring (not shown). FIG. 20e shows the device of FIG. 20d after withdrawal of the device from the injection site, with the skin sensor element extending from the housing. Extension of the skin sensor releases a needle retraction mechanism (not shown) that pulls the cartridge back to its initial position within the housing, which withdraws the needle back inside the housing. FIG. 20f shows the device of FIG. 20e with the needle retracted inside the housing.

It should be clear that the embodiments described are just examples of devices in accordance with the invention. Modifications can be made and alternative specific mechanisms used for locking and releasing the components of the device during use. For example, the locking balls 17 could be replaced by locking latches on the inner housing. The needle safety spring may be retained in a compressed condition before use and released by movement of a locking latch when the cartridge is moved forwards through the inner housing. Different arrangements for the relative direction of travel of the needle and the expansion of the stored energy source can be foreseen. These and other modifications could easily be foreseen by a skilled person.

The invention claimed is:

1. An automatic drug delivery device comprising:
a housing;
a skin sensor element coupled to the housing and movable relative to the housing, wherein the skin sensor element is biased into a front position relative to the housing and is movable to a rear position relative to the housing when the skin sensor element is pressed against an injection site;
a needle assembly comprising a hypodermic needle, the hypodermic needle extending outside of the housing when the device is in a needle insertion configuration;
a drug delivery mechanism comprising a first stored energy source, within the housing;
wherein the skin sensor element and the drug delivery mechanism are configured such that movement of the skin sensor element from the front position towards the rear position causes release of the drug delivery mechanism and wherein the first stored energy source is arranged to expand along an axis that is offset from an axis of travel of the needle assembly in use;
a needle retraction mechanism configured to withdraw the hypodermic needle into the housing when the needle retraction mechanism is released;
wherein the needle retraction mechanism is coupled to the skin sensor element such that when the skin sensor element is moved from the rear position towards the front position, and the needle is in the needle insertion position, the needle retraction mechanism is released.

2. An automatic drug delivery device according to claim 1, comprising a skin sensor biasing element configured to move the skin sensor element from the rear position towards the front position when the skin sensor element is removed from the injection site.

3. An automatic drug delivery device according to claim 1, wherein the drug delivery mechanism is prevented from being released until the skin sensor element is moved from the front position towards the rear position.

4. An automatic drug delivery device according to claim 1, wherein the drug delivery mechanism prevents release of the needle retraction mechanism until the needle is in the needle insertion position.

5. An automatic drug delivery device according to claim 1, wherein the drug delivery mechanism comprises a further stored energy source that, in operation, is released to deliver a drug through the hypodermic needle.

6. An automatic drug delivery device according to claim 1, wherein the device is configured so that the first stored energy source is used both to move the hypodermic needle from an initial position to an insertion position and to deliver the drug through the hypodermic needle.

7. An automatic drug delivery device according to claim 1, wherein the needle assembly comprises a drug container containing a drug for injection.

8. An automatic drug delivery device according to claim 7, wherein the needle assembly comprises a plunger rod, wherein the drug delivery mechanism is configured to move the needle and drug container to the insertion position and subsequently to move the plunger rod relative to the drug container to deliver the drug.

9. An automatic drug delivery device according to claim 1, wherein in operation the drug delivery mechanism moves the needle assembly from an initial position to an insertion position, and wherein when the needle assembly is in the insertion position and the skin sensor element is moved from the rear position towards the front position, the needle assembly is uncoupled from the first stored energy source of the drug delivery mechanism.

10. An automatic drug delivery device according to claim 9, wherein the drug delivery mechanism comprises a drive member positioned between the first stored energy source and the needle assembly.

11. An automatic drug delivery device according to claim 10, wherein the drive member comprises a resilient portion and engages the needle assembly to drive the needle assembly to a needle insertion position, and wherein the resilient portion is deflected to disengage the drive member from the needle assembly when the needle assembly reaches the insertion position and the skin sensor element is moved from the rear position to the front position, so as to uncouple the first stored energy source from the needle assembly.

12. An automatic drug delivery device according to claim 10, wherein the drive member comprises a resilient portion and engages the needle assembly to drive the needle assembly to a needle insertion position, and wherein the resilient portion is prevented from being deflected to disengage the drive member from the needle assembly by the housing or by the skin sensor element until the needle assembly reaches the insertion position and the skin sensor element is moved from the rear position towards the front position.

13. An automatic drug delivery device according to claim 1, wherein the needle retraction mechanism comprises a second stored energy source configured to withdraw the hypodermic needle into the housing.

14. An automatic drug delivery device according to claim 13, wherein the second stored energy source is restrained from retracting the needle by the first stored energy source.

15. An automatic drug delivery device according to claim 13, wherein the first stored energy source transfers energy to the second stored energy source as the needle is moved to the needle insertion position.

16. An automatic drug delivery device according to claim 15, wherein the second stored energy source is a spring that is compressed by the drug delivery mechanism as the needle assembly is moved to the insertion position.

17. An automatic drug delivery device according to claim 13, wherein the second stored energy source is released by the drug delivery mechanism as the needle assembly is moved to the insertion position.

18. An automatic drug delivery device according to claim 11, wherein the drug delivery mechanism is restrained from release by a coupling between the drug delivery mechanism and the housing, and wherein the coupling is released when the skin sensor element is in the rear position.

19. An automatic drug delivery device according to claim 18, wherein a drive component of the drug delivery mechanism is restrained relative to a portion of the housing by a locking member engaging a portion of the drive component.

20. An automatic drug delivery device according to claim 19, wherein the locking member is restrained from moving out of engagement with the drive component by the skin sensor element until the skin sensor element is moved towards the rear position.

21. An automatic drug delivery device according to claim 17, wherein when the skin sensor element is in the rear position, an aperture in the skin sensor element or a discontinuation of a locking surface on the skin sensor element, aligns with the locking member, allowing the locking member to move out of the engagement with the drive component.

22. An automatic drug delivery device according to claim 16, wherein the locking member comprises a plurality of balls, each ball engaged with a recess in the drive component and in an aperture in an inner portion of the housing to restrain the drug delivery mechanism from moving relative to the housing.

23. An automatic drug delivery device according to claim 19, wherein the drive component is the drive member.

24. An automatic drug delivery device according to claim 11, wherein the drive member comprises a spring seat and an engagement portion configured to engage the needle assembly, wherein the spring seat and the engagement portion are connected by the resilient portion.

25. An automatic drug delivery device according to claim 24, wherein the resilient portion comprises one or more resilient arms.

26. An automatic drug delivery device according to claim 25, wherein the resilient arms are configured to flex in a direction orthogonal to a direction of travel of the needle assembly from an initial position to the needle insertion position.

27. An automatic drug delivery device according to claim 24, wherein the drive member comprises a plurality of spring seats and plurality of engagement portions, each spring seat connected to an engagement portion by one or more resilient arms.

28. An automatic drug delivery device according to claim 24, wherein the first stored energy source provides the energy to deliver the drug, and wherein the engagement portions engage a plunger rod, the plunger rod being configured to move within a drug container to deliver the drug through the hypodermic needle.

29. An automatic drug delivery device according to claim 24, wherein the resilient portion is be held in tension by the first stored energy source as the needle assembly moves to the needle insertion position.

30. An automatic drug delivery device according to claim 11, wherein the drive member comprises at least two resilient arms extending on opposite sides of needle assembly and at least one spring seat connected to the resilient arms and engaging the first stored energy source of the drug delivery mechanism.

31. An automatic drug delivery device according to claim 11, wherein the needle assembly comprises a cam surface that engages the drive member to ensure disengagement of the needle assembly from the drive member when the resilient portion is allowed to deform.

32. An automatic drug delivery device according to claim 31, wherein a cam surface is provided to engage with each of the engagement portions of the drive member.

33. An automatic drug delivery device according to claim 31, wherein each of the cam surfaces on the needle assembly abut an engagement portion of the drive member an angle oblique to a direction of travel of the needle assembly from the initial position to the insertion position relative to the housing, so that when the one or resilient arms is allowed to flex, the action of the first stored energy source or the second stored energy source, or both the first stored energy source and the second stored energy source, forces the needle assembly to disengage from the drive member.

34. An automatic drug delivery device according to claim 1, wherein the first stored energy source is arranged within the housing so that needle travels through or past at least a portion of the first stored energy source as it is withdrawn into the housing.

35. An automatic drug delivery device according to claim 34, wherein the first stored energy source comprises first and second drive springs arranged on opposite sides of the needle assembly when the needle is in a retracted position.

36. An automatic drug delivery device according to claim 35, wherein the needle retraction assembly comprises a second stored energy source which is a spring arranged to expand in a space between the drive springs.

37. An automatic drug delivery device according to claim 1, wherein the drug delivery device is an autoinjector.

* * * * *